United States Patent [19]

Jones et al.

[11] Patent Number: 4,924,574
[45] Date of Patent: May 15, 1990

[54] SIZING UNIT FOR CUTTING STOMA WAFERS

[75] Inventors: Orville F. Jones; Robert C. Simpson, both of Bettendorf, Iowa

[73] Assignee: O.S.T., Ltd., Bettendorf, Iowa

[21] Appl. No.: 380,410

[22] Filed: Jul. 17, 1989

[51] Int. Cl.$^5$ ............................................. B26B 3/00
[52] U.S. Cl. ...................................... 30/115; 30/358; 30/361; 83/953; 83/829; 83/468.7
[58] Field of Search ............... 83/467 R, 454, 522, 83/684, 686, 925 R, 926 R, 829; 604/332, 338; 30/278, 280, 282, 283, 286, 289, 290, 115, 316, 358, 361; 408/204, 207, 67, 68

[56] References Cited

U.S. PATENT DOCUMENTS 2,487,542 11/1944 Haff ........................................ 83/454
3,329,051 7/1967 Derwin ................................. 83/684
4,753,010 6/1988 Franovich ............................. 83/686
4,817,287 4/1989 Arnold et al. ........................ 30/316

Primary Examiner—Douglas D. Watts
Assistant Examiner—Hwei-Siu Payer
Attorney, Agent, or Firm—Henderson & Sturm

[57] ABSTRACT

The disclosed unit is for use in improving the stoma wafer or face plate of an appliance worn by ostomates following surgery for ileostomy and the like. The unit comprises a base having a flat top surface which receives the wafer flat-wise thereon in a predetermined position relative to a gage which is engageable by a circular cutter that cuts a circular opening or hole in the center of the wafer, the diameter of the hole corresponding to a prior measurement of the diameter of the particular stoma. The gage is adjustably carried by the base to accommodate cutters of various diameters so as to enhance the versatility of the unit.

14 Claims, 2 Drawing Sheets

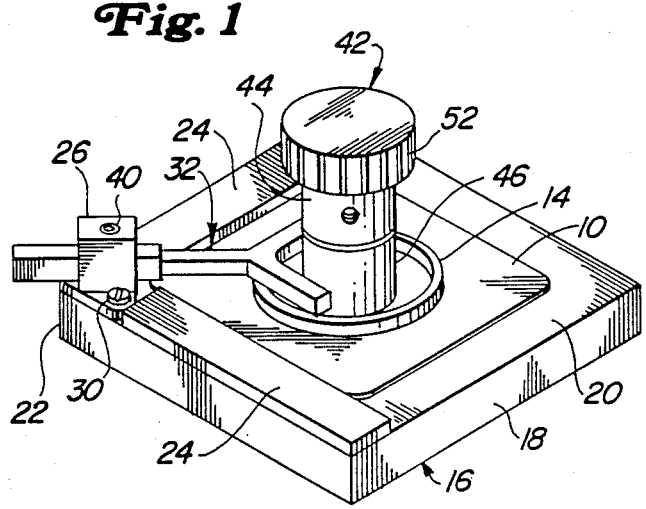
Fig. 1
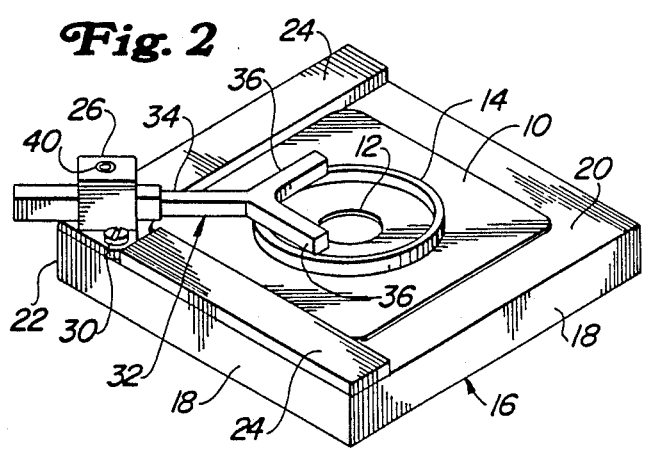
Fig. 2
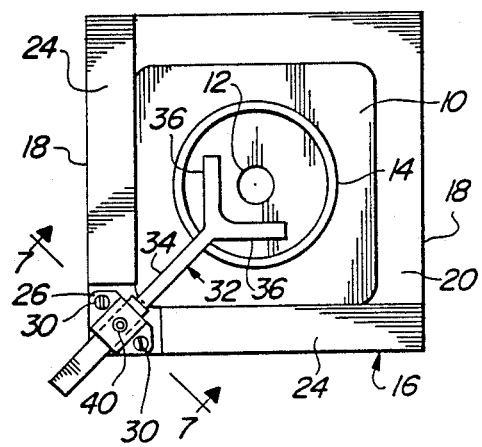
Fig. 3
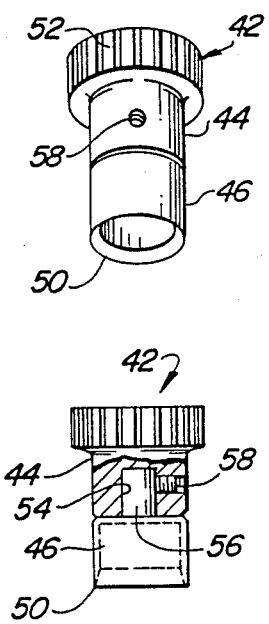
Fig. 5
Fig. 6
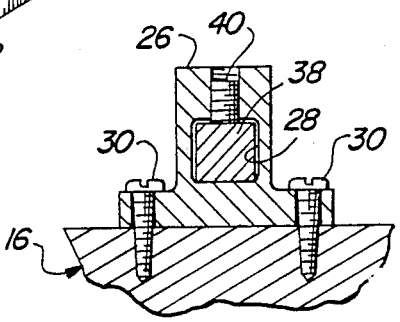
Fig. 7
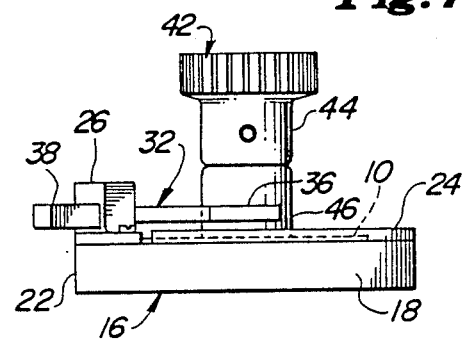
Fig. 4

SIZING UNIT FOR CUTTING STOMA WAFERS

BACKGROUND AND SUMMARY OF THE INVENTION

A typical stoma appliance comprises a face-plate or wafer adhesively applied to the user's peristomal skin and having an opening or hole at which the stoma is exposed. The wafer includes a ring or flange to which a pouch is detachably connected for receiving ileac waste. Most wafers are provided with a starter hole too small for immediate use but which must be enlarged according to the diameter of the stoma. Enlargement of the hole is usually accomplished by the use of scissors with curved blades. Because of the relatively wide variations in stoma diameters it is not feasible to manufacture and sell wafers according to different stoma diameters. Thus, the "popular" system is for the user to purchase wafers and cut holes according to his particular situation.

A major problem that results from scissor-cutting of the stoma hole is that the hole is usually not only inaccurately sized as to diameter but it frequently has ragged edges which permit leakage between the back face of the wafer and the peristomal skin and ileac waste migrates outwardly from the stoma and causes disintegration of the seal between the wafer and the skin. This of course requires early replacement of the wafer and increases the user's costs and the need for scissor-cutting of a hole in the replacement wafer.

According to the present invention, a low-cost sizing unit is provided in the form of a kit or fixture for sale to ostomates to be used by them for cutting accurate circular holes in stoma wafers by means of a base having a flat top on which the wafer is placed flatwise to be cut at its center by an accurately gaged circular cutter which centers on the center of the wafer and cuts a hole according to the dimension of the user's stoma. It is a feature of the invention that the base includes locator means for accurately positioning the wafer relative to a gage adjustably located with respect to the wafer center. The adjustability of the gage accommodates cutters of different diameters.

The unit components are formed of materials having the characteristics of long-life, low cost and easy maintenance. The cutter is preferably made of two parts, a manually engageable body and a separable cutting element enabling interchangeability of several cutters while retaining the main body, thus further lowering the purchase price of the unit.

Further features and advantages of the invention will appear as a preferred embodiment of the invention is disclosed in the ensuing description and accompanying drawings.

DESCRIPTION OF THE DRAWINGS

FIG. 1 is a prespective of the complete unit, showing a stoma wafer and a cutter in operating position.

FIG. 2 is a similar view but with the cutter removed.

FIG. 3 is a plan view of the unit, also without the cutter.

FIG. 4 is a side view of the unit, with the cutter in place.

FIG. 5 is a perspective of the assembled cutter.

FIG. 6 is an elevation of the cutter with portions broken away to show the interior structure.

FIG. 7 is a section on the line 7—7 of FIG. 3.

DETAILED DESCRIPTION OF A PREFERRED EMBODIMENT OF THE INVENTION

Figure 8:
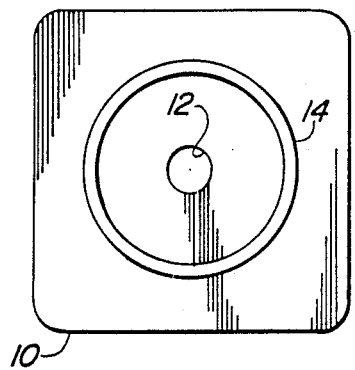
FIG. 8 is a face view of a stoma wafer having a starter hole.

Reference will be had first to FIG. 8 for a brief description of a stoma wafer 10, typically square with rounded corners and having a starter or pilot hole 12 centered within a circular ring or flange 14 to which the appliance pouch (not shown) is attachable. Wafers or plates are commonly furnished in several sizes; e.g., four, five and six-inch squares of relatively thin, film-like material of suitable plastic or like composition. To prepare the wafer for use, whether with or without the starter hole, the user first accurately measures his stoma as to diameter and, then, with scissors, cuts a circular (or near circular) hole centered in the face of the wafer and having a diameter somewhat larger in diameter than the diameter of his stoma. Current recommendations are that the hole should be about one-eighth to one-quarter of an inch larger than the stoma diameter. The need for accuracy in cutting the hole is seen in the requirement that the wafer-to-skin seal be as near perfect as possible and further that the configuration be such as not to irritate the stoma or the surrounding skin.

The sizing unit includes a base 16, here made of hardwood such as oak, maple, etc., and preferably having a square shape wherein the sides or edges of the square provide marginal portions 18 delineating a flat top surface area 20 for receiving the stoma wafer 10 flatwise thereon. Along two of the sides or edges 18 that meet at a corner 22 the base has rigid thereon locator means in the form of upstanding ribs or strips 24 that are abutted by two edges of the wafer for accurately positioning the wafer on the base top. The base area exceeds that of a four-inch wafer so as to accommodate larger-area wafers. In this respect, it should be noted that the locator strips will accommodate circular or part-circular wafers because of the geometrical relationship between two sides a right angle (as at the corner of the strips 24) and an arc about a radius and tangent to those sides. The center of the wafer will lie on a line that bisects the angle between the locator strips, which in this case is a diagonal of the square base and wafer.

The base carries, at the corner where the locator strips meet, a support 26 which is configured to provide a socket 28. The support is attached to the base as by screws 30 and the support is accurately positioned on the base so that the center line of the socket is vertically coplanar with the diagonal referred to above. In the present case, the socket is square in cross section (FIG. 7) for receiving and supporting gage means 32 of Y-shaped configuration and having a leg 34 an inner portion made up of and a pair of arms 36 integral with the leg and disposed at right angles to each other. The leg of course lies along the afore-said diagonal and its end remote from the arms 36 is formed as a square shank 38 snugly but slidably received in the support socket 28 for selective adjustment along the diagonal. A set screw 40 cooperates between the support and shank for fixing the selected position of the gage. Since the socket and shank are square, the gage is not rotatable about its lengthwise axis and thus the gage arms will be horizontally coplanar with the base top and stoma face.

Figure 9:
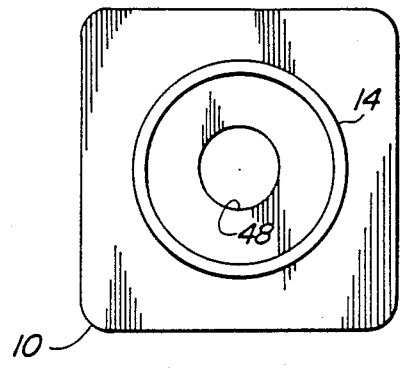
FIG. 9 shows the stoma wafer with a larger stoma hole.

The unit is furnished by the supplier with the gage means set at a situs according to the directions of the ultimate user in which situs the arms are centered on the centerline of the wafer, or coaxial with the starter hole 12, which, being too small (one-half inch or so) for use as a stoma hole, must be enlarged This function is achieved here by a cutter element 42, here made up of an upper part or body 44 and a lower part 46, both of which are preferably cylindrical. In this case, the lower part is gaged by the gage means by being tangently received between the gage means arms 36 which thus center the cutter on the axis or vertical centerline of the starter or pilot hole. In the case of a wafer without the starter hole, the cutter will center on the exact center of the wafer area. In either instance, the cutter will cut into the wafer to form a circular stoma hole or opening 48 (FIG. 9) of a size determined by a lower cutting edge 50 on the cutter lower part 46, the cutting edge diameter and the setting of the gage means having been selected according to the user's prior measurement of his stoma. The top part of the cutter is provided with grooves or equivalent gripping portions 52 to improve the handgrip of the user for rotating the cutter.

The cutter parts are separably interconnected, as by a socket 54 in the body and a lug or projection 56 on the lower part, these being preferably square in cross-section. A set screw 58 is used as releasable means to connect and disconnect the parts.

The use and operation of the unit will have been clear from the foregoing. It should be observed that shapes and dimensions have been used in somewhat specific senses in the interests of clarity and convenience and may be varied within wide limits without departing from the spirit and scope of the invention.

We claim:

1. A sizing unit for cutting a circular central opening in a stoma wafer having a vertical center line, comprising: a base having a flat top surface area dimensioned to receive a stoma wafer flat-wise thereon and further having marginal portions laterally outwardly of said area, locator means on at least one of the marginal portions adapted to engage the wafer for positioning the wafer on said area, a support on one of the marginal portions, gage means carried by the support and projecting laterally over and in spaced relation above said area and having an inner portion adapted to center on the vertical center line of the wafer, and a cutter element of cylindrical configuration on a vertical axis and engageable with the gage means inner portion to dispose said axis coaxially with said center line of the wafer, said cutter element having a coaxial, lower, circular cutting edge for cutting a central, circular opening in the wafer.

2. A sizing unit according to claim 1, in which the cutter element comprises coaxially related and separably interconnected upper and lower parts, the lower part having the circular cutting edge and the upper part projecting upwardly past the gage means inner portion and serving as a handle.

3. A sizing unit according to claim 1, in which the gage means is carried by the support for selective lateral adjustment for varying the location of the inner portion of the gage relative to the center of the wafer.

4. A sizing unit according to claim 3, in which the support includes a horizontal socket, the gage means includes a horizontal portion slidably received by the socket, and releasable securing means cooperates between said portion and the support for selectively positioning the gage.

5. A sizing unit according to claim 4, in which the gage means is a y-shaped element as seen in plane, having a leg providing the socket received horizontal portion and a pair of arms related to each other at substantially a right angle and providing the inner portion of the gage means for engaging the cutter element.

6. A sizing unit according to claim 1, in which two of the marginal portions of the base are disposed at a right angle to each other and meet at a corner, the locator means comprises ribs disposed respectively along said marginal portions, the gage means support is located at said corner, and the gage means projects over the top of the base generally along a line that bisects the angle between the locator ribs.

7. A sizing unit according to claim 6, in which the gage means is carried by the support for selective adjustment along said line of projection.

8. A sizing unit according to claim 7, in which the gage means is y-shaped as seen in plan, having a leg and a pair of arms, the leg is disposed diagonally and the arms are related to each other at substantially a right angle and form the gage means inner portion for engaging the cutter element.

9. For use in a sizing unit for cutting a circular central opening in a stoma wafer having a vertical center line, the combination of a base member having a flat top surface area dimensioned to receive a stoma wafer flatwise thereon and further having marginal portions laterally outwardly of said area, locator means on at least one of the marginal portions adapted to engage the wafer for positioning the wafer on said area, a support on one of the marginal portions, and gage means carried by the support and projecting laterally over and in spaced relation above said area and having an inner portion adapted to center on the vertical center line of the wafer.

10. The combination according to claim 9, in which the gage means is carried by the support for selective lateral adjustment for varying the location of the inner portion of the gage relative to the center of the wafer.

11. The combination according to claim 10, in which the support includes a horizontal socket, the gage means includes a horizontal portion slidably received by the socket, and releasable securing means cooperates between said portion and the support for selective positioning the gage.

12. The combination according to claim 11, in which the gage means is a y-shaped element as seen in plane, having a leg providing the socket received horizontal portion and a pair of arms related to each other at substantially a right angle and providing the inner portion of the gage means for engaging the cutter element.

13. The combination according to claim 9, in which two of the marginal portions of the base are disposed at a right angle to each other and meet at a corner, the locator means comprises a pair of ribs disposed respectively along said two sides, the gage means support is located at said corner, and the gage means projects over the top of the base generally along a line that bisects the angle between the locator ribs.

14. The combination according to claim 13, in which the gage means is carried by the support for selective adjustment along said line of projection.

* * * * *